US00PP12841P2

(12) United States Plant Patent
Sharma

(10) Patent No.: US PP12,841 P2
(45) Date of Patent: Aug. 13, 2002

(54) NEW GUINEA IMPATIENS PLANT NAMED 'SERENITY'

(75) Inventor: Jagan N. Sharma, San L. Obispo County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/585,561

(22) Filed: Jun. 1, 2000

(51) Int. Cl.[7] ..... A01H 5/00
(52) U.S. Cl. ..... Plt./318
(58) Field of Search ..... Plt./318

(56) References Cited

U.S. PATENT DOCUMENTS

PP9,742 P * 12/1996 Dummen ..... Plt./318
PP10,048 P * 9/1997 Trees ..... Plt./318
PP11,710 P * 12/2000 Klemm ..... Plt./318

* cited by examiner

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A distinct cultivar of Impatiens plant named Serenity, characterized by its orange flower color, deep green leaves, early flowering, long-lasting flowering, and self-branching and vigorous mounded growth habit.

1 Drawing Sheet

1

The present invention relates to a new and distinctive cultivar of Impatiens plant, botanically known as Impatiens, commercially known as New Guinea Impatiens, and known by the cultivar name 'Serenity'. 'Serenity' was developed in a controlled breeding program by crossing Waller Seedling No. 96-2E-110-17 (seed parent) with Waller Seedling No. 95-1E-15 (pollen parent). Both parents are proprietary breeding lines which have not been sold or made publicly available in this country.

Asexual reproduction carried out in Lompoc, Calif. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known to the inventor and used in the floriculture industry:

1. 'Serenity' has orange flowers of Red Group 40A with 'Antigua' (U.S. Plant Pat. No. 8,283) having Red Group 41A colored flowers and 'Celebration Orange' (U.S. Plant Pat. No. 10,078) having Orange-Red Group 33A colored flowers.
2. The flower diameter of 'Serenity' is similar to 'Antigua' (6.5 to 7.0 cm) but smaller than 'Celebration Orange' (7.5 to 8.0 cm).
3. 'Serenity' has smaller leaves at 9 to 10 cm in length than 'Antigua' (11 to 12 cm long) and 'Celebration Orange' (13 to 14 cm long).
4. The spurs of 'Serenity' are red-purple with green tips while both 'Antigua' and 'Celebration Orange' have red-purple spurs with red-purple tips.
5. 'Serenity' has a green pedicel with a faint red-purple cast near the flower end, while 'Antigua' has a moderate red-purple cast on the entire pedicel, and 'Celebration Orange' has a heavy red-purple cast on the pedicel.
6. 'Serenity' has a green midrib on the underside of the leaf while 'Antigua' and 'Celebration Orange' both have red-purple midribs on the leaves.
7. 'Serenity' has the least amount of anthocyanin pigment in stems with 'Antigua' having the most.
8. 'Serenity' has a more mounded growth habit than either of 'Antigua' or 'Celebration Orange' which are both more upright in habit.

2

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary dictionary significance are used.

Botanical classification: *Impatiens hawkeri.*

Parentage: A controlled cross between female parent Waller Seedling No. 96-2E-110-17 and male parent Waller Seedling No. 95-1E-15.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fibrous.

Plant description:

*Form and habit of growth.*—Mounded to semi-upright, self-branching, intermediate to semi-tall in height, (25–30 cm high; 34–40 cm wide) flowers open over the top of leaf canopy; continuous flowering; vigorous growing "flowering herb" (a non-woody stemmed plant that dies completely at the end of the growing season). Lateral branches: length of 15–20 cm (highly variable), diameter of 4–6 cm, Yellow-Green Group 146A with Greyed-Purple Group 184A cast, internode length of 6–8 cm; Stem: length of 20–28 cm (highly variable), diameter of 6–8 mm, Yellow-Green Group 146A with Greyed-Purple Group 184A cast.

*Foliage description.*—Deep green with light green midrib and no leaf variegation. (1) Size: 9 to 10 cm long and 3.0 to 3.5 cm wide on average mature leaf. (2) Shape: Lanceolate with acuminate apex and acute base. (3) Texture: Both upper and lower surfaces are glabrous. (4) Margin: Finely serrated with fine ciliate. (5) Color: Young foliage, top side is Yellow-Green Group 146A, underside is Yellow-Green Group 146B. Mature foliage, top side is Yellow-Green Group 147A, underside is Yellow-Green Group 147B. (6) Venation: Pinnate, light green in color. (8) Leaf arrangement: Whorl-usually 5 leaves in a whorl. (9) Petiole: Length of 1.5–2 mm, diameter of 2 mm, Yellow-Green Group 146D with Greyed-Purple Group 185D cast.

Flowering description:

*Flowering habits.*—Flowers continuously from leaf whorl in a progressively orderly manner with one flower per leaf axil. When the last flower in a whorl opens the first flower in the leaf whorl above starts to open. It takes 5 to 7 days for a mature bud to fully open and the flower may last two weeks or longer depending on the environment.

*Natural flowering season.*—Indeterminant and continuous; quantity of flowering increases with increasing levels of light.

*Flower bud.*—Ellipsoidal; flowers perfect; spur is colored Greyed-Purple Group 184B with a Yellow-Green Group 147A tip and is 5.0 cm long on average on mature bud, with the throat behind the ovary and originating from the major sepal. Length: 18–20 mm just before opening. Diameter: 12 mm. Color: Red Group 40A just before opening.

*Flowers borne.*—On individual pedicels 4.5 cm long which are Yellow-Green Group 146D in color with a slight Greyed-Purple Group 184C cast near flower end from a whorl of usually five leaves. Flowering progressively around the whorls as buds and leaves develop. Leaf axils have one flower each.

*Quantity of flowers.*—Numerous because of self-branching nature of plant and the long-lasting flower characteristic.

*Diameter of flower.*—6.5 to 7.0 cm.

*Petals.*—(1) Shape: Heart; standard is largest. (2) Color: Top side when opening is Red Group 40A with no fading; underside is Red Group 40C. The eye of the flower is Red-Purple Group 63A with a lighter area of Red-Purple Group 63B that shades to Red Group 40A. (3) Number of petals: Five. (4) Size of petals: Standard: 4.5 cm wide by 3.0 cm long, two equal lobes with moderate cut. Wings: 3.5 cm wide by 3.0 cm long, two unequal lobes with moderate cut. Keel: 4.0 cm wide and 3.0 cm long, two unequal lobes with moderate cut. (5) Texture: Smooth, satin-like.

*Reproductive organs.*—(1) Stamens: Five in number. (a) Anther: Hooded shape, color is Yellow-White Group 158C with a Red Group 40B tint. (b) Pollen color: Yellow-White Group 158C. (2) Pistils: (a) Stigma: Five segmented column, White Group 155C in color. (b) Style color: White Group 155C. (c) Ovaries: Five in number, size is 6 mm when immature, color is Yellow-Green Group 146A.

Disease resistance: No significant disease or insect problems seen to date.

Fruit/seed production: Plants are fertile but do not normally set seed under greenhouse or garden conditions unless in a controlled breeding program.

OTHER IMPORTANT CHARACTERISTICS

1. Minimal fading of older flowers, large overlapping petals result in a round flower that produces an attractive floral display.

2. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus extending the growing season.

3. Is a self-branching, early flowering, vigorous growing plant that can quickly finish in a 15 to 25 cm container.

I claim:

1. A new and distinct variety of Impatiens plant named 'Serenity', as illustrated and described.

* * * * *

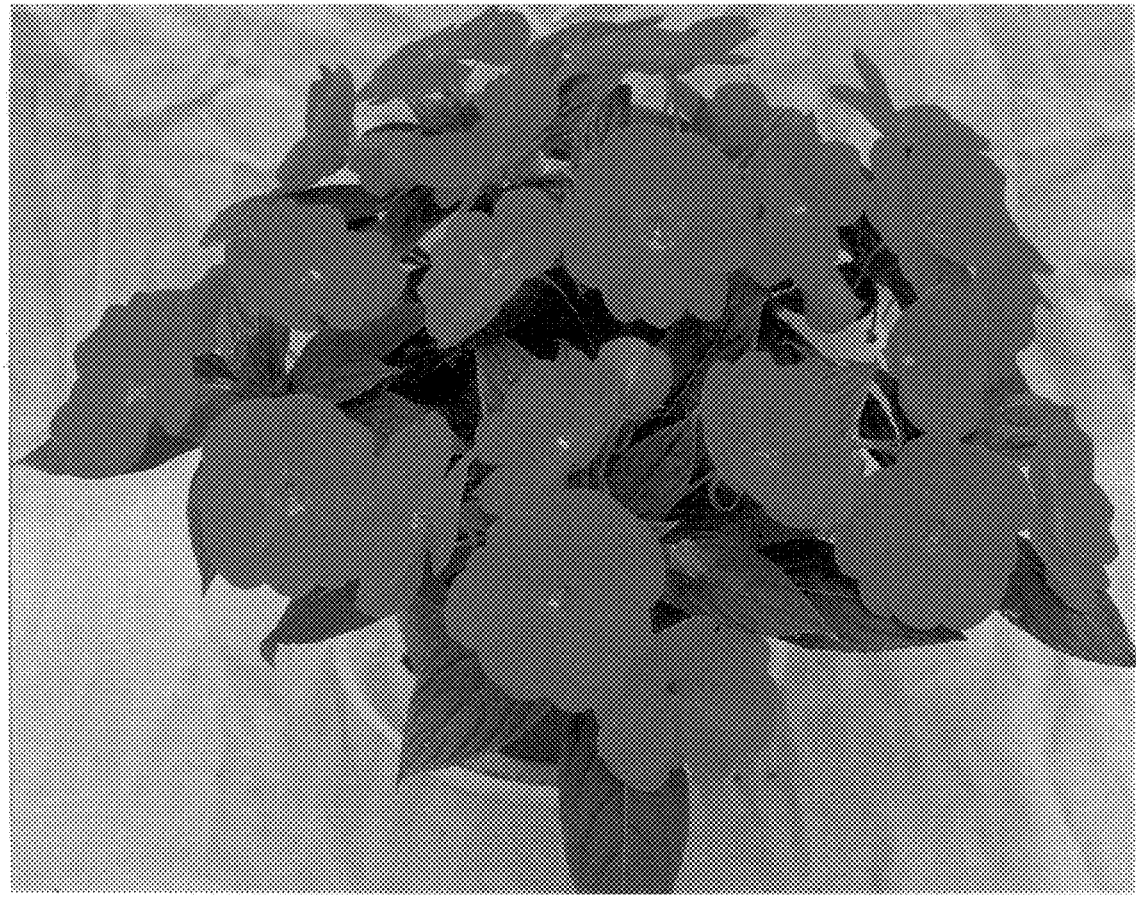

UNITED STATES PATENT AND TRADEMARK OFFICE

CERTIFICATE OF CORRECTION

PATENT NO. : PP12,841 P2
DATED : August 13, 2002
INVENTOR(S) : Jagan N. Sharma

It is certified that error appears in the above-identified patent and that said Letters Patent is hereby corrected as shown below:

Title page,
Item, [73], Assignee, "Oglevee, Ltd., Connellsville, PA (US)" should read
-- Waller Genetics Incorporated, Guadalupe, CA (US) --

Column 2,
Line 35, "34-40" should read -- 35-40 --.

Signed and Sealed this

Twenty-first Day of January, 2003

JAMES E. ROGAN
*Director of the United States Patent and Trademark Office*